United States Patent
Colbaugh

(10) Patent No.: US 9,138,554 B2
(45) Date of Patent: Sep. 22, 2015

(54) PATIENT INTERFACE DEVICE WITH SINGLE-SIDED NASAL COMPONENT

(75) Inventor: Michael Edward Colbaugh, Level Green, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 420 days.

(21) Appl. No.: 13/509,315

(22) PCT Filed: Oct. 15, 2010

(86) PCT No.: PCT/IB2010/054688
§ 371 (c)(1),
(2), (4) Date: May 11, 2012

(87) PCT Pub. No.: WO2011/061648
PCT Pub. Date: May 26, 2011

(65) Prior Publication Data
US 2012/0222678 A1    Sep. 6, 2012

Related U.S. Application Data

(60) Provisional application No. 61/263,428, filed on Nov. 23, 2009.

(51) Int. Cl.
*A61M 15/08*    (2006.01)
*A62B 7/00*    (2006.01)
*A61M 16/06*    (2006.01)

(52) U.S. Cl.
CPC ....... *A61M 16/0666* (2013.01); *A61M 16/0683* (2013.01); *A61M 16/0694* (2014.02)

(58) Field of Classification Search
USPC ............................ 128/207.18, 207.13, 206.11
See application file for complete search history.

(56) References Cited

U.S. PATENT DOCUMENTS

| | | |
|---|---|---|
| 4,273,124 A | 6/1981 | Zimmerman |
| 4,660,555 A | 4/1987 | Payton |
| 8,127,767 B2 * | 3/2012 | Mutti et al. ............... 128/207.18 |
| 2005/0028823 A1 * | 2/2005 | Wood ....................... 128/207.18 |
| 2005/0121037 A1 | 6/2005 | Wood |
| 2008/0092905 A1 * | 4/2008 | Gunaratnam et al. ... 128/207.18 |
| 2008/0149105 A1 | 6/2008 | Matula |
| 2008/0223375 A1 | 9/2008 | Cortez |

FOREIGN PATENT DOCUMENTS

| | | |
|---|---|---|
| CN | 2546045 Y | 4/2003 |
| WO | WO2005014080 A2 | 2/2005 |
| WO | WO2005079726 A1 | 9/2005 |
| WO | WO2007041786 A1 | 4/2007 |
| WO | WO2008060523 A2 | 5/2008 |

\* cited by examiner

*Primary Examiner* — Kristen Matter
(74) *Attorney, Agent, or Firm* — Michael W. Haas

(57) ABSTRACT

A patient interface device (2) includes a coupling (4) structured to receive and distribute a flow of breathing gas (100), and a nasal component (6) extending outwardly from the coupling. The nasal component includes a single sealing element (8) structured to engage and seal only one of the two nostrils (306, 308) of a nose (304) of a patient (300). A method of fitting the patient interface device includes receiving the aforementioned patient interface device, and engaging and sealing a single nostril of the patient's nose with the single sealing element.

7 Claims, 8 Drawing Sheets ered by a patient, and wherein the second extension extends laterally outwardly from the coupling for attachment of the corresponding one of the straps on the other side of the face of the patient.

PATIENT INTERFACE DEVICE WITH SINGLE-SIDED NASAL COMPONENT

CROSS-REFERENCE TO RELATED APPLICATIONS

This patent application claims the priority benefit under 35 U.S.C. §119(e) of U.S. Provisional Application No. 61/263,428 filed on Nov. 23, 2009, the contents of which are herein incorporated by reference.

BACKGROUND OF THE INVENTION

1. Field of the Disclosure

The disclosed concept relates to patient interface devices, and, in particular, to a patient interface device including a single-sided nasal component for selectively sealing only one of the two nostrils of a patient's nose.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder such as, for example, upper airway resistance syndrome (UARS), congestive heart failure, and sleep disordered breathing (SDB), such as snoring, hypopnea, and sleep apnea syndrome, in particular, obstructive sleep apnea (OSA).

Non-invasive ventilation and pressure support therapies involve the placement of a patient interface device including a mask component on the face of a patient. The mask component may be, for example and without limitation, a nasal mask that covers the patient's nose, an open interface such as a nasal cushion or cannula having nasal prongs that are received within the patient's nostrils, a nasal/oral mask that covers both the nose and the mouth, or a full face mask that covers the patient's face. The patient interface device interfaces a flow generator, such as a ventilator or pressure support device, with the airway of the patient, so that a flow of breathing gas can be delivered from the pressure/flow generating device to the airway of the patient.

A common complaint about patient interface devices is that the mask component is confining, claustrophobic and/or obtrusive to the user. Open interfaces such as, for example and without limitation, nasal cannuli and various nasal pillows or cushions, are typically smaller and, therefore, less obtrusive. However, disadvantages associated with such open interfaces include the fact that the air flow can be uncomfortably cool, and can dry the patient's nasal and sinus passages. Additionally, open interfaces do not pressurize the upper airway passages as much as a pressure-controlled sealed interface.

SUMMARY OF THE INVENTION

In one embodiment, a patient interface device is provided that includes a coupling structured to receive and distribute a flow of breathing gas, and a nasal component extending outwardly from the coupling, the nasal component including a single sealing element structured to engage and seal only one of the two nostrils of a nose of a patient.

In one particular embodiment, the patient interface device may further include a mounting apparatus structured to secure the patient interface device in a desired orientation with respect to the nose of the patient. The mounting apparatus may include a strap, and the coupling may include an attachment portion, wherein the strap is attached to the attachment portion. The attachment portion may include a first extension and a second extension, wherein the first extension extends laterally outwardly from the coupling for attachment of a corresponding one of the straps on one side of the face of the patient, and wherein the second extension extends laterally outwardly from the coupling for attachment of the corresponding one of the straps on the other side of the face of the patient.

A method of fitting a patient interface device is also provided. The method includes receiving the patient interface device, wherein the patient interface device includes: (i) a coupling for receiving and distributing a flow of breathing gas; and (ii) a nasal component extending outwardly from the coupling, the nasal component including a single sealing element. The method further includes engaging and sealing a single nostril of a nose of a patient with the single sealing element. The patient interface device may also include at least one conduit, and the method may include the step of coupling the conduit to the coupling of the patient interface device to deliver the flow of breathing gas from a flow generator to the patient interface device. Preferably the nasal component of the patient interface device is pivotally coupled to the coupling of the patient interface device.

These and other objects, features, and characteristics of the disclosed concept, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosed concept. As used in the specification and in the claims, the singular form of "a", "an", and "the" include plural referents unless the context clearly dictates otherwise.

Figure 1:
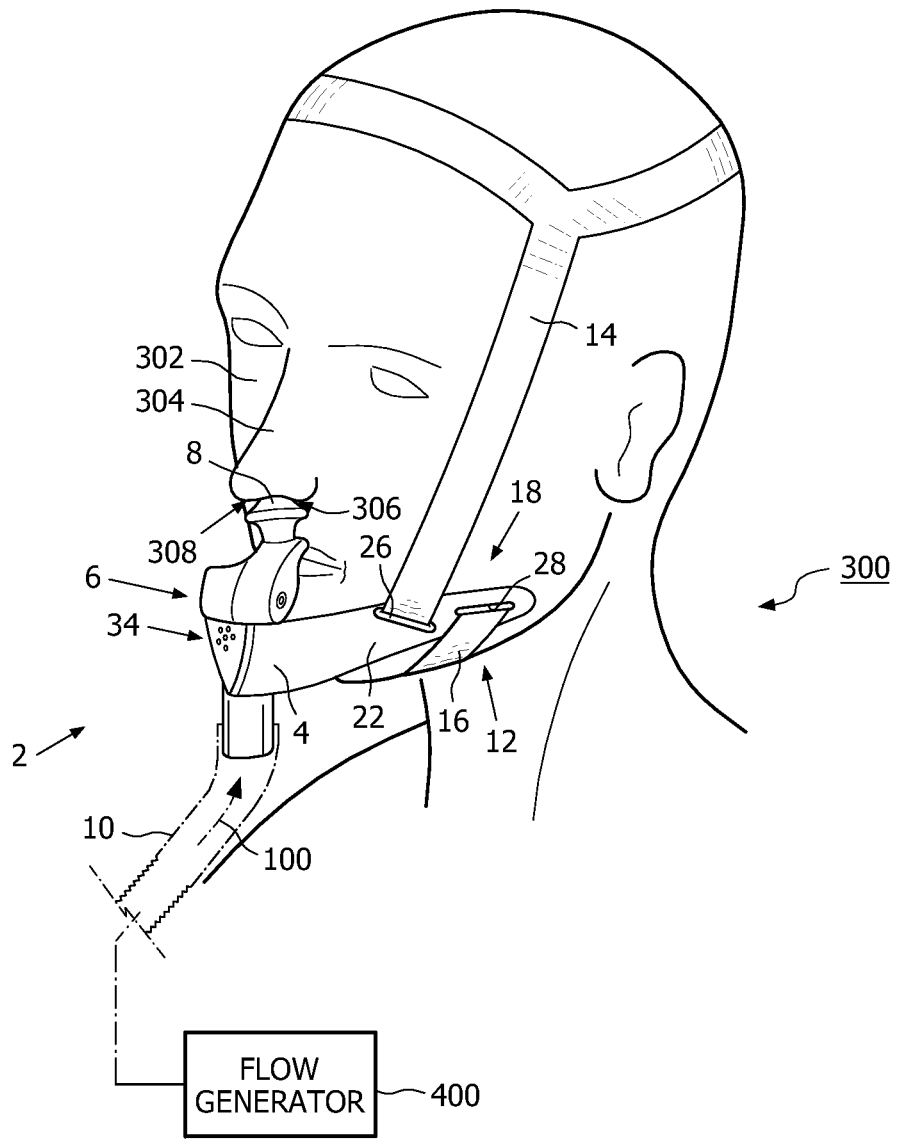
FIG. 1 is a perspective view of a patient interface device according to one particular embodiment of the disclosed concept, with the patient interface device being shown as employed by a patient.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As employed herein, the terms "nostril", "nare", and "naris" are used substantially interchangeably to refer to one of the nasal passageways or airways of the nose of a patient. As employed, herein, the statement that two or more parts or components are "coupled" together shall mean that the parts are joined or operate together either directly or through one or more intermediate parts or components. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

DETAILED DESCRIPTION OF EXEMPLARY EMBODIMENTS

FIG. 1 shows patient interface device 2 in accordance with one non-limiting embodiment of the disclosed concept. Patient interface device 2 includes a coupling component 4 (referred to herein as simply a "coupling") and a nasal component 6, which extends outwardly therefrom. Nasal component 6 includes a single sealing element 8, which may comprise, for example and without limitation, a nasal pillow or cushion, a nasal insert, a cannula, a nasal mask or any other known or suitable alternative apparatus for providing a suitable sealed interface with an airway (e.g., nasal passage, naris, nostril) of a patient 300. When patient interface 2 is employed, single sealing element 8 engages and seals only one nostril 106 of the two nostrils 106, 108 of nose 104 of patient 100, as shown.

Patient interface 2 further includes at least one conduit 10 (partially shown in phantom line drawing in FIG. 1; see also conduit 110 partially shown in solid line drawing in FIGS. 3 and 4, and conduit 210 of FIG. 5) for delivering a flow of breathing gas (indicated generally by arrow 100 shown in phantom line drawing in FIG. 1) from a flow generator 400 (shown in simplified form in FIG. 1) to coupling 4 of patient interface device 2 which, in turn, receives and selectively distributes flow of breathing gas 100 to one single nostril 306 of nose 304 of patient 300. In this manner, patient interface device 2 overcomes the disadvantages of known patient interface devices (e.g., without limitation, open interfaces such as, for example, a cannula; and closed interfaces, such as, for example, a CPAP mask). That is, patient interface device 2 and, in particular, single-sided nasal component 4 thereof, enables the other nostril 308 of patient's nose 304 to be unobstructed for unencumbered exhalation and inhalation, for example, of ambient air. Accordingly, single-sided nasal component 6 enables the sinus cavities of patient 300 to be re-warmed and moisturized, thereby improving the comfort of patient 300 while receiving ventilation therapy. As an added benefit, patient interface device 2 also minimizes audible noise, such as noise caused by patient 300 breathing against air pressure or flow when exhaling.

It will be appreciated that the disclosed concept of selectively sealing only one single nostril 306 of nose 304 of patient 300 can be employed with any known or suitable type and/or configuration of patient interface device other than those which are shown and described herein. It will further be appreciated that the disclosed concept can be employed in combination with a wide variety of additional or alternative features to provide any known or suitable type of ventilation support (e.g., without limitation, pressure support) to the desired airway of patient 300. For example and without limitation, in the example of FIG. 1, nasal component 6 is pivotally coupled to coupling 4, although such a feature is not required. Similarly, coupling 4 is shown to include exhalation port 34 in FIG. 1. However, such exhalation port 34 is not required, or it could alternatively, or additionally, be disposed on nasal component 6 or some other suitable location on patient interface device 2. In addition, exhalation port 34 can have any one of a variety of configurations, including those found on existing patient interface devices. Other elements, such as filters, ports, sensors, and any other conventional elements employed on or for use with patient interface devices can be used in combination with patient interface device 2.

Figure 2:
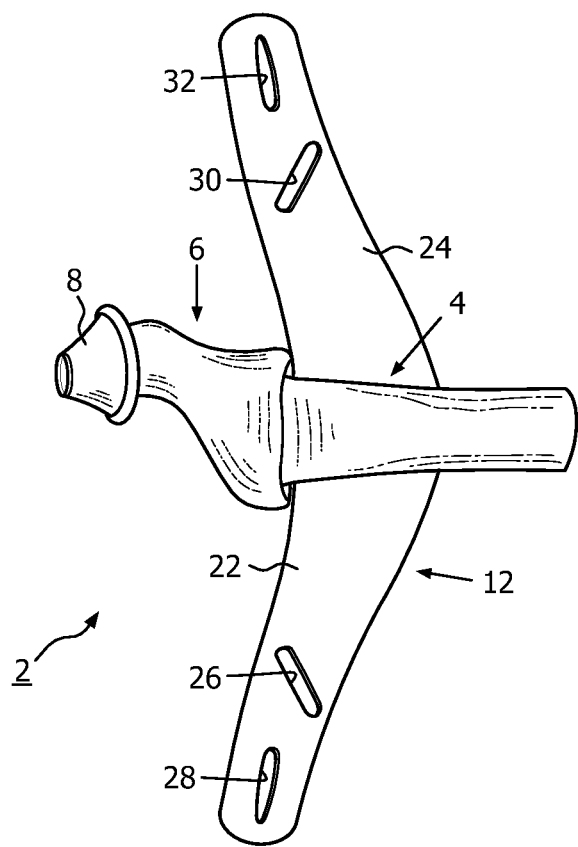
FIG. 2 is front view of the underside of a portion of the patient interface device of FIG. 1.

Continuing to refer to FIG. 1, it will be appreciated that patient interface device 2 further includes a mounting apparatus 12 such as, for example and without limitation, an adjustable head strap 14 and an adjustable chin strap 16, which are shown, in order to secure patient interface device 2 in a desired orientation with respect to nose 304 of patient 300. As best shown in FIG. 2 of exemplary patient interface device 2 includes an attachment portion 18 having a first extension 22 and a second extension 24. First extension 22 extends laterally outwardly from coupling 4 for attachment of a corresponding one of straps 14,16 on one side of the patient's face 302, and second extension 24 extends laterally outwardly from coupling 4 in the opposite direction for attachment of the corresponding one of straps 14,16 on the other side of patient's face 302. In the example of FIG. 1, first extension 22 and second extension 24 include first slots 26, 30 respectively, to receive corresponding portions of adjustable head strap 14, and second slots 28,32, respectively, to receive corresponding portions of adjustable chin strap 16. It will, however, be appreciated that any known or suitable alternative number, type and/or configuration of mounting apparatus 12 could be employed, without departing from the scope of the disclosed concept. See, e.g., the patient interface device shown in FIGS. 1-2 is disclosed in U.S. patent application Ser. No. 11/811,126 (publication no. 2008/0149105), the contents of which are incorporated herein by reference.

Figure 3:
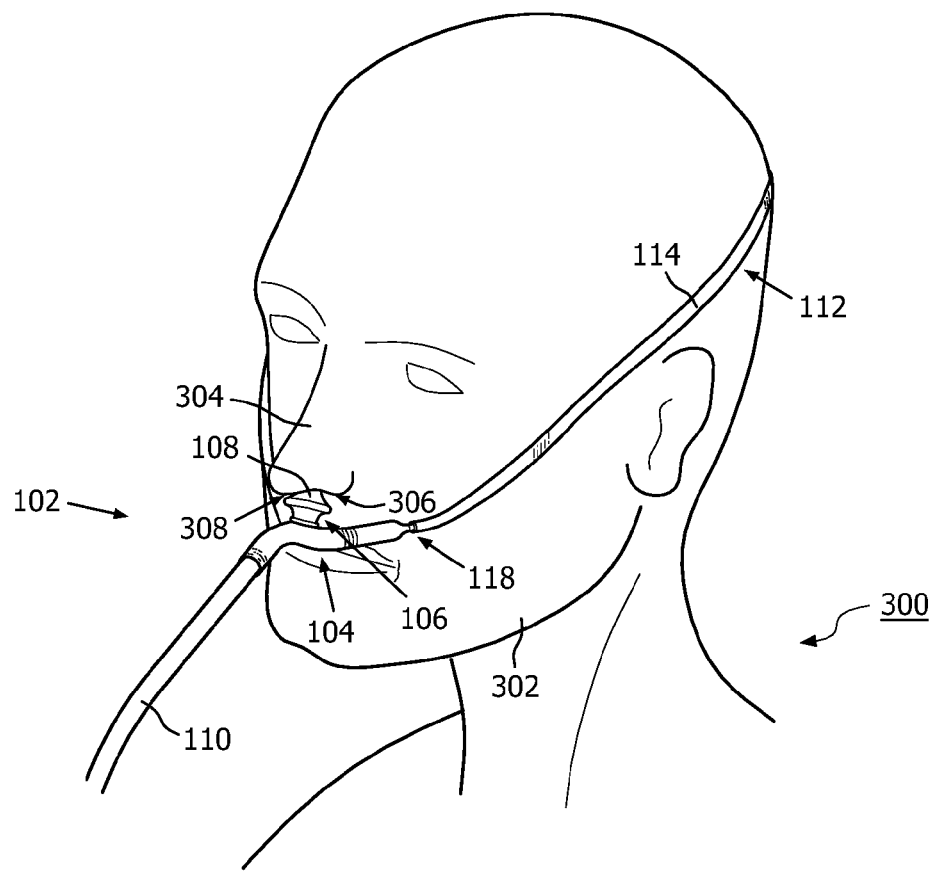
FIG. 3 is a perspective view of a patient interface device according to another particular embodiment of the disclosed concept.
Figure 4:
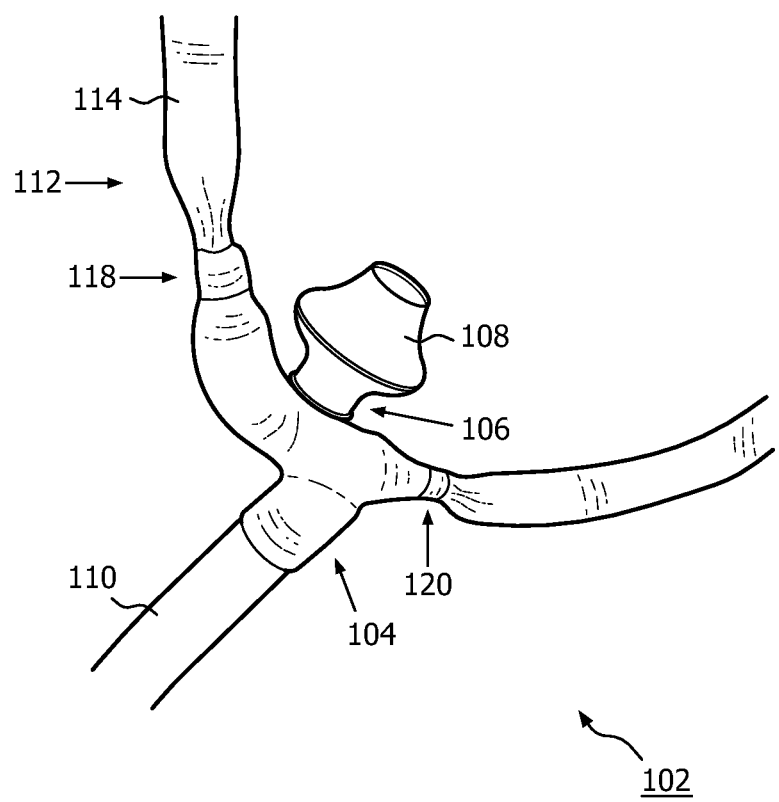
FIG. 4 is a perspective view of the underside of a portion of the patient interface device of FIG. 3.
Figure 5:
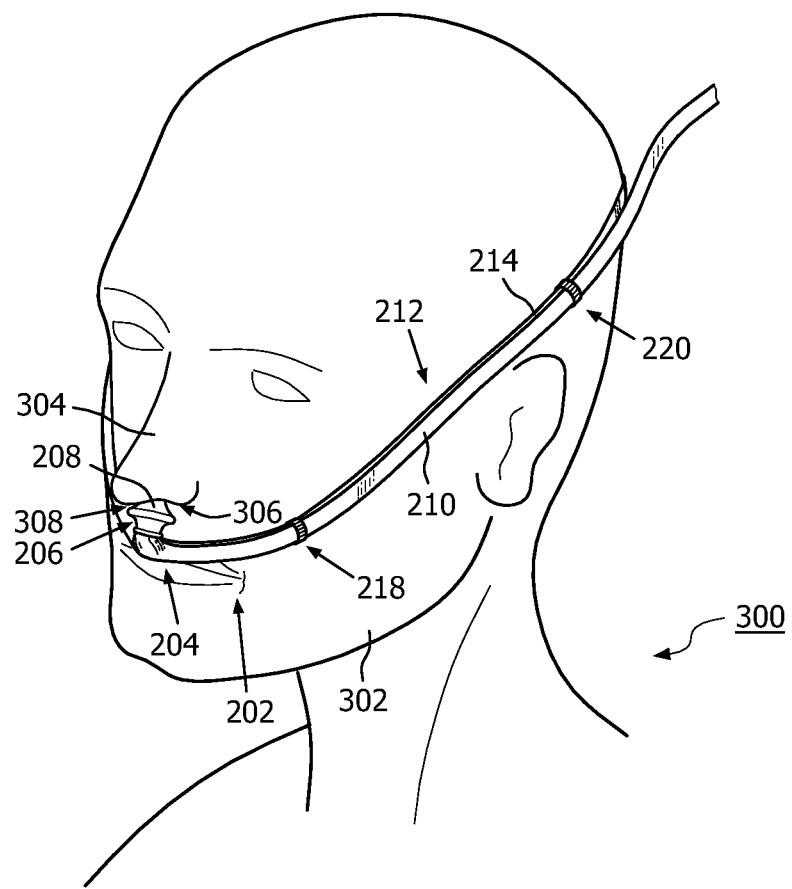
FIG. 5 is a perspective view of a patient interface device according to another particular embodiment of the disclosed concept.

For example and without limitation, FIGS. 3-5, respectively, show two non-limiting alternative patient interface device embodiments in accordance with the principles of the present invention. In particular, the embodiments of FIGS. 3-5 illustrate how minimal the structure of patient interface device 102 (FIGS. 3 and 4), 202 (FIG. 5) can be. Thus, it will be appreciated that in accordance with the disclosed concept, an effective pressure or flow interface is provided in a minimally invasive or obtrusive manner. Furthermore, patient comfort is enhanced by virtue of the fact that one of patient's nostrils 308 remains unencumbered and, therefore, free to inhale and exhale to keep patient's sinus cavities warm and moist.

In the example of FIGS. 3 and 4, patient interface device 102 includes a coupling 104 and nasal component 6, which extends outwardly therefrom and includes a single sealing element 108. Single sealing element 108 engages and seals corresponding single nostril 306 of patient's nose 304. Conduit 110 is structured to be coupled to coupling 104 to provide fluid communication with flow generator (not shown, but see flow generator 400, shown in simplified form in FIG. 1). Mounting apparatus 112 of patient interface device 102 includes a head strap 114, which is suitably attached to coupling 104 at attachment portions 118 and 120. It will be appreciated that while exemplary single sealing element 108 is shown to be a nasal pillow or cushion, that any other known or suitable alternative sealing element (e.g., without limitation, nasal insert; cannula; nares—external mask envelope) or method (e.g., without limitation, adhesives; suction; pressure against a flexible member) could be employed, without departing from the scope of the disclosed concept.

In the example of FIG. 5, patient interface device 204 includes an even more minimalistic (e.g., compact; non-obtrusive) design in which a conduit 210 extends outwardly from a coupling 204 and is secured by attachment portions 218, 220 (e.g., without limitation, straps; ties) of head strap 14 of mounting apparatus 12. In this manner, conduit 210 extends along side strap 214 adjacent patient's face 302. Nasal component 206 and, in particular, single sealing element 208 thereof, extend outwardly from coupling 4 to engage and seal only one corresponding nostril 306 of patient's nose 304. It will be appreciated that single sealing element 208, nasal component 206, coupling 204 and/or conduit 210, or any combination thereof, could, although need not necessarily, comprise one single continuous piece of suitable material (e.g., without limitation, plastic, silicon, gel, or rubber).

Figure 6:
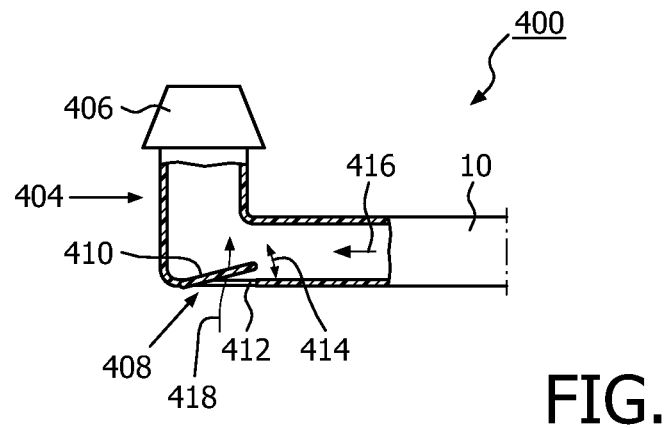
FIG. 6 is a partial sectional view of a patient interface device according to another embodiment of the present invention.

Referring now to FIG. 6, there is shown a patient interface device 400 according to a further embodiment of the present invention. More specifically, in this exemplary embodiment, patient interface 400 includes a coupling component 404 and a nasal component 406, in which a valve element 408 is provided in the coupling components. Valve element 408 is a one-way valve having a valve flap 410 that selectively opens and closes opening 412 as indicated by arrow 414. Valve flap 410 is coupled to coupling component 404 in any suitable manner so that it is biased into the closed position during exhalation and is open during at least a portion of the inhalation phase of the respiratory cycle. A spring for living hinge, for example, can be used to couple valve flap 410 to coupling component 404.

In use, valve element 408 opens to atmosphere using inspiration so that the user receives a flow of gas from both the supply of gas delivered via conduit 10, as indicated by arrow 416 and the supply of gas entering the patient interface device via valve element 408, as indicated by arrow 418. This configuration is beneficial in situations where the use may not receive an adequate supply of gas from the gas supply alone. Suppose, for example, that a user is receiving a fixed flow rate of gas 416 in his or her left nostril and the rest of the gas he/she needs during each breath from the right nostril under normal conditions. Suppose, then, that the right nostril becomes blocked, which may occur due to nasal congestions, allergies, and/or external forces, such as a pillow or mattress pushing on or blocking the right nostril. In this situation, the user's may attempt or desire to inhale more gas than is being provided by gas flow 416 alone. In which case, valve flap 410 would open during inhalation, due to the reduced pressure within coupling portion 404 relative to ambient atmospheric pressure, thereby allowing a secondary flow of gas 418 to be provided to the user's left nostril.

While a single valve element is shown in FIG. 6 having single flap configuration, it is to be understood that the present invention contemplates providing additional valve elements. Also, the valve element can have other configurations, such as a butterfly valve, a ball valve, etc. Finally, the valve element can be provided at other locations on the patient interface device and/or conduit 10 so long as it allows for additional gas flow into the patient interface device when gas flow 416 is not sufficient to meet the patient's demand. It is to be understood that valve element 408 can be provided in addition to exhaust port 34.

Figure 7A:
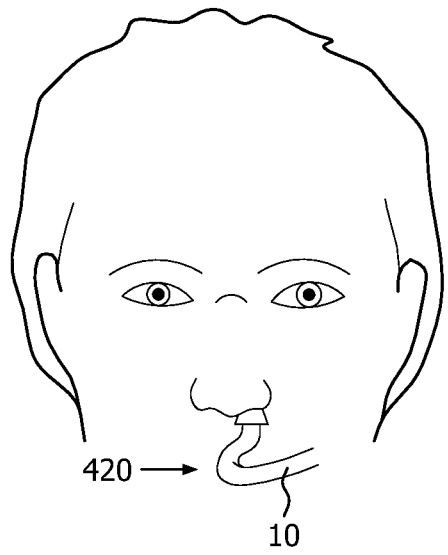
FIGS. 7A and 7B are front views showing a patient interface device according to yet another embodiment of the present invention that is reversible with respect to its placement on the user.
Figure 7B:
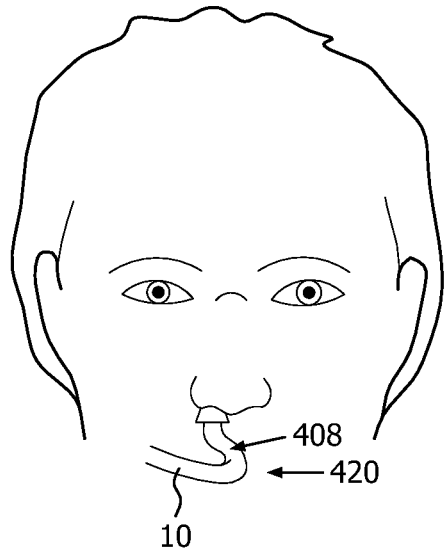

FIGS. 7A and 7B illustrate another embodiment of a patient interface device 420 according to the principles of the present invention. In this embodiment, patient interface device 420 is reversible with respect to its placement on the user so that the user can select which nostril is sealed by nasal component 406 depending on the orientation of the patient interface device. In other words, patient interface device 420 is configured that it can be placed on the user so as to seal either the left nostril (FIG. 7A) when placed on the patient in a first position, or seal the right nostril (FIG. 7B) when placed on the patient in a second position, which is the reversed, "flipped", or mirror image of the first position. That is, when a first side of patient interface device 420 is facing a patient as shown in FIG. 7A, nasal component 406 seals the left nostril. When patient interface device 420 is flipped over and worn the other way, nasal component 406 engages and seals a right nostril, with the first side 408 of the patient interface device now facing away from such a patient.

It can thus be appreciated that this embodiment of the present invention allows the user to select which nostril to seal and does so merely by changing how he/she wears the patient interface device. Of course, suitable headgear couplings must be provided on the patient interface device to allow the user to choose either orientation for the wearing of the patient interface device.

Figure 8A:
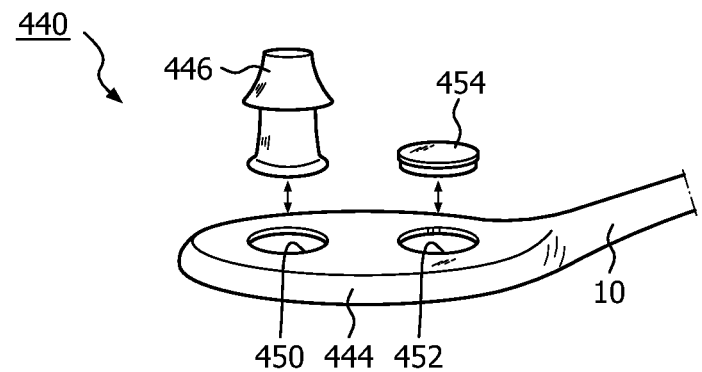
FIGS. 8A and 8B are front views showing a patient interface device according to still further embodiment of the present invention that also provides the ability to select which nostril to engage and seal.
Figure 8B:
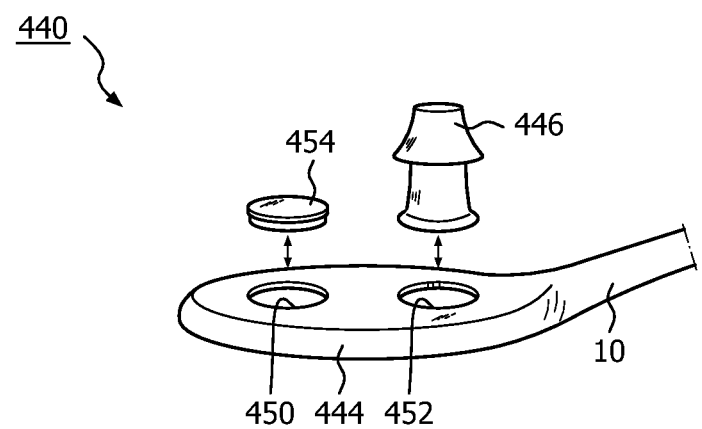

FIGS. 8A and 8B show a patient interface device 440 according to still further embodiment of the present invention that also provides the ability to select which nostril to engage and seal. In this embodiment, the user need not change the orientation of the patient interface device as in the embodiment of FIGS. 7A and 7B, but instead changes the physical configuration of the patient interface device. To this end, patient interface device 440 includes a first port 450 and a second port 452 provided in coupling 444. In a first configuration shown in FIG. 8A, which is used to seal a first nostril, a nasal component 446 is selectively coupled to first port 450 and second port 452 is blocked via a plug 454. In a second configuration, shown in FIG. 8B, which is used to seal a second nostril, nasal component 446 selectively coupled to the second port 452 and first port 450 is blocked with plug 454. This embodiment of the present invention allows the user to set up or configure patient interface device 440 so that the nasal component engages and seals the nostril of their choosing.

While FIGS. 8A and 8B illustrate one exemplary technique and configuration for the ports, plug, and nasal component, it can be appreciated that the present invention contemplates a wide variety of techniques and configurations for these components. For example, the plug and nasal component can be formed from a unitary structure that is reversed or turned to provide the two different configuration.

Figure 9:
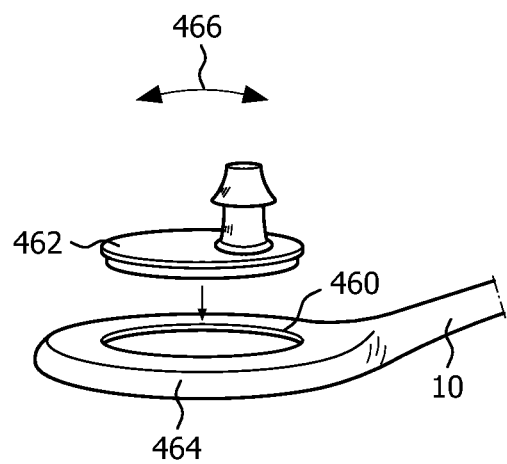
FIG. 9 illustrates a further embodiment of a patient interface device that also provides the ability to select which nostril to engage and seal.

As shown in FIG. 9, the present invention further contemplates that coupling 444 can include a single port 460 defined in coupling 464, with a single nasal component 462 being adapted to be selectively disposed in port 460. When nasal component 462 is asymmetrical so that when the nasal component is disposed in port 460 in a first configuration, the nasal component seals a first nostril, and when nasal component 462 is flipped or reversed, as indicated by arrow 464, so that it is disposed in a second configuration, the nasal component 4 seals a second nostril.

While only a few of the different possible techniques have been disclosed for altering the position of the nasal component so that the user can select which nare to seal, it is to be understood that the present invention contemplates a wide variety of other techniques for controlling or changing the position of the nasal component to provide this user selectivity. For example, conduit 10 can be selectively attachable to either side of the coupling portion with the other side being blocked to change the orientation of the nasal component.

Figure 10:
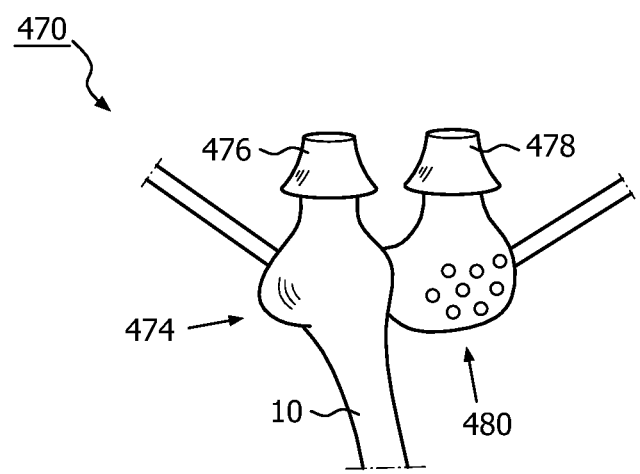
FIG. 10 is sectional view of a further embodiment of the present invention.

FIG. 10 illustrates a still further embodiment of the present invention. In this embodiment, patient interface device 470 includes a coupling component 474 and a nasal component 476, and a stabilizing component 478. Nasal component 476 serves the function of the nasal components discussed above, i.e., to engage an seal one of the nares of the user. Stabilizing component 478 engages the other nostril but it does so to further the purpose of providing a stable patient interface on the face and user; and does not seal, i.e., is does not communicate a flow of gas carried by conduit 10 to an airway of the user. Instead, stabilizing component 478 is open to atmosphere, for example, by providing an exhaust vent or port 480. Gas carried by conduit 10 does not enter stabilizing component 478, e.g., there is a wall or other physical barrier between each side of coupling component 474.

Port 480 can have any configuration, size, shape, and location, so long as it provides a suitable communication of stabilizing component 478 to ambient atmosphere. The present invention further contemplates that port 480 can be configured and arranged to suit any desired structural and flow characteristics. For example, in one embodiment, port 480 is configured and arranged so as to minimize flow resistance, thereby providing a relatively open communication between the nares of the user and the ambient atmosphere.

Although the disclosed concept has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface device for delivering a flow of breathing gas to a patient having a face, nose, and two nostrils, the patient interface device comprising:
   a coupling structured to receive and distribute the flow of breathing gas, wherein the coupling includes a first port and a second port spaced from the first port on a top surface of the coupling;
   a conduit extending from the coupling to deliver the flow of breathing gas from a flow generator to the patient interface device;
   a nasal pillow component sized and configured to be selectively inserted into and held by either the first port or the second port to enable the flow of breathing gas to be delivered through the nasal pillow component; and
   a plug member sized and configured to be selectively inserted into and held by either the first port or the second port to block the first port or the second port.

2. The patient interface device according to claim 1, further comprising a mounting apparatus structured to secure the patient interface device in a desired orientation with respect to a nose of the patient.

3. The patient interface device according to claim 2, wherein the mounting apparatus includes a strap.

4. A patient interface device for delivering a flow of breathing gas to a patient having a face, nose, and two nostrils, the patient interface device comprising:
   a coupling structured to receive and distribute the flow of breathing gas, wherein the coupling includes an oblong port on a top surface of the coupling, the coupling having a first coupling end and a second coupling end opposite the first coupling end;
   a conduit extending from the coupling to deliver the flow of breathing gas from a flow generator to the patient interface device; and
   an oblong asymmetrical nasal component sized and configured to be selectively inserted into and held by the oblong port, wherein the nasal component has a first end and a second end opposite the first end, and a single nasal sealing member positioned a first distance from the first end of the nasal component and a second distance from the second end of the nasal component, the first distance being greater than the second distance such that the nasal component is adapted to selectively engage the oblong port in a first configuration in which the nasal sealing member is closer to the first coupling end than the second coupling end and is structured to seal a first one of the two nostrils and in a second configuration in which the nasal sealing member is closer to the second coupling end than the first coupling end and is structured to seal a second one of the two nostrils.

5. The patient interface device according to claim 4, wherein the single nasal sealing member is one of a nasal pillow, a nasal insert, a cannula, and a nasal cushion.

6. The patient interface device according to claim 4, wherein at least one of the coupling and the nasal component further includes an exhalation port.

7. The patient interface device according to claim 4, further comprising a one-way valve operatively coupled to the coupling, the nasal component, or both, and wherein the one-way valve includes a valve flap biased into a closed position during exhalation and structured to be moved to an open position wherein the valve flap moves toward an interior of the coupling or the nasal component during at least a portion of the inspiratory cycle.

* * * * *